United States Patent [19]

Scheuffgen et al.

[11] Patent Number: 4,612,192

[45] Date of Patent: Sep. 16, 1986

[54] OIL COMPONENTS FOR COSMETICS AND PHARMACEUTICALS

[75] Inventors: Ingeborg Scheuffgen, Neuss; Alfred Meffert, Monheim, both of Fed. Rep. of Germany

[73] Assignee: Henkel Kommanditgesellschaft auf Aktien, Duesseldorf, Fed. Rep. of Germany

[21] Appl. No.: 630,060

[22] Filed: Jul. 12, 1984

[30] Foreign Application Priority Data

Jul. 22, 1983 [DE] Fed. Rep. of Germany ....... 3326455

[51] Int. Cl.$^4$ .................. A61K 7/027; A61K 7/06; A61K 7/021; C11C 3/00
[52] U.S. Cl. .................. 424/70; 260/410.7; 424/63; 424/64; 514/548
[58] Field of Search ............... 260/410.7; 424/312, 424/64, 63, 70

[56] References Cited

U.S. PATENT DOCUMENTS

| | | | |
|---|---|---|---|
| 2,806,842 | 9/1957 | Gerecht et al. | 424/70 |
| 3,035,069 | 5/1962 | Findley et al. | 260/410.7 |
| 3,066,159 | 11/1962 | DeGroote et al. | 260/410.7 |
| 3,182,034 | 5/1965 | Van Hook | 260/410.7 |
| 3,262,953 | 7/1966 | Findley et al. | 260/410.7 |
| 3,335,053 | 8/1967 | Weitzel | 424/64 |
| 3,592,940 | 7/1971 | Quesada | 424/64 |
| 3,934,003 | 1/1976 | Tums et al. | 424/70 |
| 4,001,141 | 1/1977 | Kalopissis et al. | 424/64 |
| 4,224,311 | 9/1980 | Vanlerberghe et al. | 424/64 |
| 4,399,313 | 8/1983 | Vanlerberghe et al. | 424/70 |
| 4,488,564 | 12/1984 | Grallier et al. | 424/70 |

OTHER PUBLICATIONS

A. Streituiesar Jr. and C. Heathcock, *Intro to Organic Chemistry*, 1976, MacMillan Pub. Co.; pp. 648–652.
Findley, Swern, Scanlan, "Epoxidation of Unsaturated Fatty Materials with Peracetic Acid in Glacial Acetic Acid Solution", *Journal of the American Chemical Society*, vol. 67, (Mar. 1945), pp. 412–414.

*Primary Examiner*—J. E. Evans
*Attorney, Agent, or Firm*—Ernest G. Szoke; Henry E. Millson, Jr.; Mark A. Greenfield

[57] ABSTRACT

New oil components for cosmetic and pharmaceutical applications consist of reaction products of epoxidized triglyceride oils with monohydric alcohols containing from 1 to 4 carbon atoms. The oil components are produced by reacting an epoxidized triglyceride oil containing from about 4 to about 8% by weight of epoxide oxygen, preferably an epoxidized soya bean oil containing from about 6 to about 7% by weight of epoxide oxygen, in the presence of an acidic catalyst with a monohydric $C_1$–$C_4$-alcohol, preferably methanol, in excess at the boiling temperature of the alcohol until the oxirane rings have been completely opened, followed by neutralizing the catalyst and distilling off the excess alcohol. The new oil components are eminently suitable, inter alia, for the production of cosmetic stick preparations.

8 Claims, No Drawings

OIL COMPONENTS FOR COSMETICS AND PHARMACEUTICALS

BACKGROUND OF THE INVENTION

1. Field of the Invention

This invention relates to new oil components for cosmetic and pharmaceutical applications.

2. Description of the Prior Art

Oily liquids of natural or synthetic origin form the basis of numerous cosmetic and pharmaceutical preparations, such as creams, ointments, oils, and stick compositions, in which they perform various functions. They are intended to make the skin smooth and supple after use, to supply it with fats after washing, to prevent it from drying out and to serve as solvents and carriers for various cosmetically and dermatologically active components and/or pigments.

The oil components used include both natural, vegetable and animal oils, such as for example olive oil, peanut oil, almond oil, jojoba oil, castor oil, mink oil, sperm oil, and also mineral oils, for example paraffin oils. Other suitable oil components are synthetic esters of natural fatty acids and monohydric or polyhydric alcohols and also modified natural substances, such as hydrogenated squalene or hydrogenated terpenes.

The natural, vegetable or animal oils contain significant quantities of unsaturated compounds. The result of this is that they change their properties under the effect of heat, atmospheric oxygen, light and moisture.

Although saturated mineral oils and synthetic oil components are stable to autoxidation and rancidity, they are often incompatible with the skin and, because of this, are also found to be unpleasant in cosmetic preparations. They often result in the undesirable development of shininess on the skin and impede its permeability to water vapor. Due to their relatively weak polarity, they also have a relatively poor dissolving effect for cosmetically and dermatologically active components.

If natural oils are saturated by hydrogenation, they lose their clear liquid character, forming stiff fats which are unsuitable for use as oil components. Triglycerides based on relatively short, saturated fatty acids which are still liquid show a viscosity that is too low for many applications. Oils distinguished by a certain viscosity coupled with a low pour point are required for the production of decorative cosmetic preparations, particularly anhydrous preparations in stick and cream form. In addition, cosmetic oil components are required to be totally compatible with the skin and mucous membrane.

DESCRIPTION OF THE INVENTION

Accordingly, the object of the present invention is to find oil components which do not have any of the disadvantages mentioned above and which show high compatibility with both the skin and mucous membrane, high stability to rancidity, high dissolving power, and also high viscosity for a low pour point.

It has been found that these requirements are met by oil components which can be obtained by reacting epoxidized triglyceride oils with monohydric alcohols containing from 1 to 4 carbon atoms.

Epoxidized triglycerides are commercially available products known as so-called epoxide plasticizers. They are obtained by epoxidizing naturally occuring unsaturated oils, such as for example soya bean oil, linseed oil, tall oil, cottonseed oil, peanut oil, palm oil, sunflower oil, rapeseed oil or neat's foot oil, with peracetic acid, for example by the process described in J. Am. Chem. Soc. 67, March 1945, pages 412–414. The epoxidation reaction converts all or some of the double bonds into oxirane rings, depending on the conversion ratio. Suitable naturally occurring triglycerides for use in preparing the epoxidized triglycerides used to prepare the oil components of the invention are those having an iodine number of from 50 to 150 which, in the event of extensive epoxidation, are converted into epoxidates having an epoxide oxygen content of from about 3 to about 10% by weight. Epoxidates having an epoxide oxygen content of from about 4 to about 8% by weight are particularly suitable for the further reaction with monohydric alcohols. The reaction with monohydric alcohols containing from 1 to 4 carbon atoms is carried out in the presence of an acidic catalyst, preferably a concentrated acid such as concentrated sulfuric acid, and results in opening of the oxirane rings with formation of

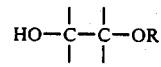

groups, wherein R is a $C_1$–$C_4$ alkyl group. The reaction is carried out with a large excess of alcohol to ensure that all the oxirane rings are quantitively opened. The alcohol is preferably used in an excess of from about 4 to about 10 moles per mole of epoxide oxygen. Suitable monohydric alcohols are, for example, methanol, ethanol, 1-propanol, isopropanol and butanol or isobutanol. The reaction temperature is preferably the boiling temperature of the alcohol. The catalyst is then neutralized with an alkaline neutralizing agent, e.g. an alkali metal methylate such as sodium methylate in methanol, and excess alcohol present is distilled off. The product is then removed, e.g. filtered from the salt resulting from neutralization of the acidic catalyst.

Liquid oil components of relatively high viscosity which are highly stable to autoxidation and rancidity and which are compatible with the skin and mucous membrane are obtained in this way. The products show high dissolving power for cosmetically and dermatologically active components and high dispersing power for pigments. Accordingly, they are eminently suitable for the production of cosmetic and pharmaceutical preparations. The oil components of the invention are used with particular advantage for the production of decorative cosmetic stick preparations, such as for example, lipsticks, makeup sticks, eyeliner and eye-shadow sticks. Sticks such as these are produced from mixtures of cosmetic oils and waxes. To establish the necessary consistency and stability, fatty alcohols, emulsifiers, for example fatty acid partial glycerides, wool fat, paraffin hydrocarbons and also cosmetic pigments and, optionally, cosmetically and dermatologically active principles are additionally incorporated in them. Although stick preparations of the above type are required to show a firm consistency and stability to heat, they are also required to show good abrasion. This necessitates the addition of liquid oil components in relatively large quantities. These oil components are required to remain in the stick composition, even when present therein in large quantities. The castor oil normally used for this purpose has the disadvantage of poor stability to oxidation.

It has surprisingly been found that the oil components of the invention are capable of effectively replacing castor oil in cosmetic stick preparations. This applies in particular to the reaction product of epoxidized soya bean oil containing from about 6 to about 7% by weight of epoxide oxygen with methanol, particularly when this reaction product has an iodine number below 20. The oil components of the invention can be incorporated in stick preparations in quantities of from about 5 to about 60% by weight. Stick preparations preferably contain from about 20 to about 50% by weight of the oil components of the invention. The stick preparations thus formulated show particularly high and improved stability to oxidation in comparison with preparations containing castor oil, and are of comparable consistency, pigment distribution and mucous membrane compatibility, as well as having slightly improved skin compatibility.

The oil components of the invention also exhibit their outstanding cosmetic properties in other cosmetic and dermatological preparations, for example in ointments, creams, skin oils, lotions, bath oils, in haircare preparations, toilet waters and deodorants.

The invention is illustrated but not limited by the following Examples.

EXAMPLES

Example 1

Reaction product of soya oil epoxide with methanol 657 kg of methanol and 1.7 kg of $H_2SO_4$ (concentrated) were introduced into a reaction vessel with reflux cooling and heated under reflux to boiling temperature (approximately 65° C.). 890 kg of a commercially available soya oil epoxide (Edenol ® D 81) containing 6.3% by weight of epoxide oxygen were gradually introduced into the boiling solution. The heat of reaction kept the solution at boiling temperature. On completion of the addition, the reaction mixture was stirred for 3 hours at 65° C. It was then neutralized with 6 kg of a 30% by weight solution of sodium methylate in methanol and the excess methanol (approximately 547 kg) was completely distilled off, leaving approximately 1000 kg of the reaction product behind in the form of a pale yellow, clear liquid.

The product had the following characteristics:
Acid number (according to DGF-C-V-2): 0.2
Saponification number (according to DIN 53401): 162
Iodine number (according to DGF-C-V-11b): 14.5
Hydroxyl number (according to DGF-C-V-17a): 207
Density at 20° C. (according to DEF-C-IV-2): 1.009
Viscosity (20° C.) (Brookfield, No. 2 spindle, 10 r.p.m.): 2.36Pa.s

Example 2

Determination of the tendency to autoxidation by comparison with castor oil

The reaction product of Example 1 was stored for 40 days at 20° C. in an open vessel both in pure form and also in the form of a stick composition containing 50% by weight of the product of Example 1. Over the 40-day storage period, the peroxide number increased as a result of autoxidation. For comparison, castor oil was subjected to the storage test both in pure form and also in the form of the same stick composition containing 50% by weight of castor oil.

The stick compositions were also subjected to the storage test after the incorporation of an anti-oxidant. The anti-oxidant used was the system of 0.02% by weight of butyl hydroxy anisole (BHA) and 0.0016% by weight of citric acid.

The stick composition was made up of the following ingredients:

| | |
|---|---|
| Beeswax | 2.5% by weight |
| Carnauba wax | 7.5% by weight |
| Candellila wax | 7.5% by weight |
| Micro wax (M.p.: 72° C.) | 4.0% by weight |
| Cetyl alcohol | 2.5% by weight |
| Glycerol monoricinoleate | 13.0% by weight |
| Castor oil or product of Example 1 | 50.0% by weight |
| Paraffin oil, thickly liquid | 2.5% by weight |
| 2-octyl-1-dodecanol | 10.5% by weight |

The peroxide number was determined by Wheeler's method (DGF Standard Method C - VI 6a).

| | PO* No. (Milliequivalents of oxygen per kg) | | |
|---|---|---|---|
| Substrate | Initial value | After 20 days | After 40 days |
| Product of Example 1 (without anti-oxidant) | 2.8 | 4.5 | 7.3 |
| Castor oil (without anti-oxidant) | 2.8 | 9.9 | 23.6 |
| Stick composition containing the product of Example 1 (without anti-oxidant) | 3.8 | 7.8 | 12.4 |
| Stick composition containing castor oil (without anti-oxidant) | 6.3 | 11.0 | 16.4 |
| Stick composition containing the product of Example 1 + anti-oxidant | 4.4 | 5.8 | 6.3 |
| Stick composition containing castor oil + anti-oxidant | 5.6 | 7.8 | 12.5 |

*peroxide

It can be seen from the development of the peroxide number that the product of Example 1 and preparations containing it are more stable to autoxidation (rancidity).

Example 3

Determination of skin compatibility and comparison with castor oil

The product of Example 1 was tested in undiluted form on rabbits using the occlusion method (Patch Test according to Fed. Register Vol., No. 187, § 1500.41 (9/27/1973)). The same test was carried out with castor oil.

Result:

After a contact time of 24 hours, the product of Example 1 had produced in all the test animals slight to distinct reddening of the skin which disappeared completely in 4 to 5 days.

After a contact time of 24 hours, castor oil had produced in all the test animals distinct to severe reddening of the skin, accompanied by slight swelling in some animals. The slowly abating incompatibility reactions were still noticeable in some of the test animals on the 4th and 5th day of the test. After 7 days, none of the rabbits showed any further reaction.

Example 4

Application Examples

| 4.1 Lipstick | |
|---|---|
| Oleyl alcohol (HD-Eutanol ®)[(2)] | 20.0% by weight |
| Product of Example 1 | 25.0% by weight |
| Beeswax | 5.0% by weight |

-continued

| 4.1 Lipstick | |
|---|---|
| Carnauba wax | 8.0% by weight |
| Ozocerite (M.p.: 70-72° C.) | 11.0% by weight |
| Candelilla wax | 3.0% by weight |
| Wool fat, water-free | 8.0% by weight |
| Paraffin oil, thickly liquid | 13.0% by weight |
| TiO$_2$ C 47051[1] | 5.3% by weight |
| Red 300404[1] | 1.7% by weight |

The product was easy to compound; the pigments were thoroughly dispersed. Appearance, stability and rise melting point (70° C.) are identical with those of a stick in which castor oil was used instead of the product of Example 1.

| 4.2 Eyeliner stick | |
|---|---|
| Cetyl alcohol | 5.0% by weight |
| Product of Example 1 | 20.0% by weight |
| Oleyl alcohol (HD-Eutanol ®)[2] | 29.0% by weight |
| Glycerolmonostearate (Cutina ® GMS)[2] | 5.0% by weight |
| Beeswax | 2.0% by weight |
| Candelilla wax | 6.0% by weight |
| Carnauba wax | 6.0% by weight |
| Ozocerite (M.p. 70-72° C.) | 15.0% by weight |
| Paraffin oil, thickly liquid | 2.0% by weight |
| Pigment Ariabel Braun 300402[1] | 10.0% by weight |

The product was easy to compound; the pigment was thoroughly dispersed. Appearance, stability and rise melting point (68.5° C.) are comparable with those of a similar stick in which castor oil was used instead of the product of Example 1.

| 4.3 Eyeshadow stick | |
|---|---|
| Lauric acid hexylester (Cetiol ®A)[2] | 35.0% by weight |
| Product of Example 1 | 10.0% by weight |
| Beeswax | 6.0% by weight |
| Carnauba wax | 5.0% by weight |
| Candelilla wax | 10.0% by weight |
| Fish silver pigment (Merck) | 30.0% by weight |

-continued

| 4.3 Eyeshadow stick | |
|---|---|
| Pigment Dark Blue 300308[1] | 4.0% by weight |

(b 1) The pigments were obtained from the Williams company of Hounslow (UK).
(2) These products were obtained frm Henkel KGaA of Duesseldorf (FRG).

The product was easy to compound; the pigments were thoroughly dispersed. Appearance, stability and rise melting point (68.5° C.) are comparable with those of a stick in which castor oil was used instead of the product of Example 1.

What is claimed is:

1. In a method for treating the human skin, mucous membrane, or hair by applying thereto a cosmetic or dermatological preparation which contains an oil component, the improvement wherein the oil component is at least one reaction product of an epoxidized triglyceride oil and a $C_{1-4}$ monohydric alcohol.

2. A method in accordance with claim 1 wherein the epoxidized triglyceride oil contains from about 3 to about 10% by weight of epoxide oxygen.

3. A method in accordance with claim 1 wherein the epoxidized triglyceride oil contains from about 4 to about 8% by weight of epoxide oxygen.

4. A method in accordance with claim 1 wherein the $C_{1-4}$ alcohol is methanol.

5. A method in accordance with claim 1 wherein the epoxidized triglyceride oil is epoxidized soya bean oil containing from about 6 to about 7% epoxide oxygen.

6. In a cosmetic preparation in stick form containing at least one wax component wherein said at least one wax component is one or more of beeswax, carnauba wax, and candelilla wax, and at least one cosmetic oil, the improvement wherein the cosmetic oil comprises from about 5 to about 60% by weight of at least one reaction product of an epoxidized triglyceride oil and a $C_{1-4}$ monohydric alcohol.

7. A cosmetic preparation in accordance with claim 6 wherein from about 20 to about 50% by weight of at least one reaction product of an epoxidized triglyceride oil and a $C_{1-4}$ monohydric alcohol is present therein.

8. A cosmetic preparation in accordance with claim 6 wherein said at least one wax component is one or more of beeswax, carnauba wax, and candelilla wax.

* * * * *